United States Patent [19]
Baxter et al.

[11] Patent Number: 5,981,490
[45] Date of Patent: *Nov. 9, 1999

[54] PEPTIDYL COMPOUNDS

[75] Inventors: Andrew Douglas Baxter; John Gary Montana; David Alan Owen, all of Cambridge, United Kingdom

[73] Assignee: Darwin Discovery, Ltd., United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/725,781

[22] Filed: Oct. 4, 1996

[30] Foreign Application Priority Data

Oct. 5, 1995 [GB] United Kingdom .................. 9520354
Apr. 4, 1996 [GB] United Kingdom .................. 9607126

[51] Int. Cl.[6] .............................. A61K 38/05; C07K 5/00
[52] U.S. Cl. .............................. 514/19; 514/18; 514/389; 530/331; 564/153; 564/154; 548/301.4; 424/184.1; 424/185.1
[58] Field of Search ................................ 514/18, 19, 389; 530/331; 564/153, 154; 548/301.4; 424/184.1, 188.1

[56] References Cited

FOREIGN PATENT DOCUMENTS

| | | |
|---|---|---|
| 2156618 | 10/1994 | Canada . |
| 0126974 | 12/1984 | European Pat. Off. . |
| 8806890 | 9/1988 | WIPO . |
| 9506031 | 3/1995 | WIPO . |
| 9513289 | 5/1995 | WIPO . |
| 9611209 | 5/1995 | WIPO . |

OTHER PUBLICATIONS

Miller, R.B. et al. (1985) "Incorporation of Coordinating Amide Bond Surrogates within Mammalian Collagenase Inhibitors" Pept. Struct. Funct., Proc. Am. Pept. Symp., 9th:815–818.

Gray, R.D. et al. (1981) "Metal Binding Peptide Inhibitors of Vertebrate Collagenase" Biochemical and Biophysical Research Communication 101(4):1251–1258.

Fournie–Zaluski et al., Eur. J. Biochem 139 267–74(1984).

Spatola et al, "Chemistry & Biochemistry —Proteins" vol. 7 (Marcell Dekkes, 1983, Weinstein Ed) pp. 267–268, 338–340.

Primary Examiner—Bennett Celsa
Attorney, Agent, or Firm—Saliwanchik, Lloyd & Saliwanchik

[57] ABSTRACT

Dipeptide compounds have therapeutic utility, inter alia, as metalloproteinase and TNF inhibitors.

18 Claims, No Drawings

PEPTIDYL COMPOUNDS

FIELD OF THE INVENTION

This invention relates to a novel class of peptidyl derivatives, to processes for their preparation, and to their use in medicine.

BACKGROUND TO THE INVENTION

Metalloproteinases, (human fibroblast) collagenase, gelatinase and tumour necrosis factor (TNF) and their modes of action, and also inhibitors thereof and their clinical effects, are disclosed in WO-A-9611209(6/95), the content of which is incorporated by reference.

In normal tissues, cellular connective tissue synthesis is offset by extracellular matrix degradation, the two opposing effects existing in dynamic equilibrium. Degradation of the matrix is brought about by the action of proteinases released from resident connective tissue cells and invading inflammatory cells, and is due, in part, to the activity of at least four groups of metalloproteinases. These are the collagenases (interstitial collagenase, MMP-1; PMN collagenase, MMP-8, collagenase-3, MMP-13), the gelatinases (getatinase A, MMP-2, 72 kDa-gelatinase, Type IV collagenase; gelatinase B, MMP-9, 92 kDa-gelatinase, Type IV collagenase) the stromelysins (poteoglycanase, MMP-3, stromelysin-1, transin; stromelysin-2, MMP-10; stromelysin 3, MMP-11) and the membrane type matrix metalloproteinases (MT-1, MMP-14; MT-2, MMP-15; MT-3, MMP-16 and MT4, MMP-17). Normally this catabolic enzymes are tightly regulated at the level of their synthesis and secretion and also at the level of their extracellular activity, the latter through the action of specific inhibitors, such as TIMP (tissue inhibitors of metalloproteinase), which form inactive complexes with metalloproteinases, and more general proteinase inhibitors such as $\alpha_2$-macroglobulins.

The accelerated, uncontrolled breakdown of connective tissues by metalloproteinase catalyzed resorption of the extracellular matrix is a feature of many pathological conditions such as rheumatoid arthritis, osteoarthritis, septic arthritis, corneal, epidermal or gastric ulceration; tumour metastasis or invasion; periodontal disease, proteinuria, coronary thrombosis associated with atherosclerotic plaque rupture and bone disease. The inhibitors claimed herein may also be useful in preventing the pathological squaelae following a traumatic injury that could lead to a permanent disability. These compounds may also have utility as a means for birth control by preventing ovulation or implantation. It can be expected that the pathogenesis of such diseases is likely to be modified in a beneficial manner by the administration of metalloproteinase inhibitors and numerous compounds have been suggested for this purpose [for a general review see R C Wahl, et al Ann. Rep, Med, Chem. 25: 175–184, Academic Press Inc., San Diego (1990)].

A number of small peptide like compounds which inhibit metalloproteinaes have been described. Perhaps the most notable of these are those relating to angiotensin converting enzyme (ACE) where such agents act to block the conversion of the decapeptide angiotcnsin I to angiotensin II, a potent pressor substance. Compounds of this type are described in EP-A-0012401. Also, related mercaptoaraide peptidyl derivatives have shown ACE inhibitor activity in vitro and in vivo (H N Weller et al (1984), Biochem Biophys. Res. Comm., 125 (1):82–89).

TNF is a cytoldne which is produced initially as a cell-associated 28 kD precursor. It is released as an active, 17 kd) form (D-M Jue et al, (1990) Biochenistry, 29:8371–8377), which can mediate a large number of deleterious effects in vivo. When administered to animals or humans it causes inflammation, fever, cardiovascular effects, hemorrhage, coagulation and acute phase responses, similar to those seen during acute infections and shock states. Chronic administration can also cause cachexia and anorexia. Accumulation of excessive TNF can be lethal.

There is considerable evidence from animal model studies that blocking the effects of TNF with specific antibodies can be beneficial in acute infections, shock states, graft versus host reactions and autoimmune disease. TNF is also an autocrine growth factor for some myelomas and lymphomas and can act to inhibit normal heamatopoiesis in patients with these tumors.

Preventing the production or action of TNF is, therefore, predicted to be a potent therapeutic strategy for many inflammatory, infectious, immunological or malignant diseases. These include, but are not restricted to, septic shock, haemodynamic shock and sepsis syndrome (Mathison et al (1988) J. Clin. Invest, 81:1925–1937; Miethke et al (1992), J. Exp. Med. 175:91–98), post ischarmic reperfusion injury, malaria (Grau et al (1989), Immunol, Rev. 112:49–70); mycobacterial infection (Barnes et al (1992) Infect. Imm. 60:1441–6), meningitis, psoriasis, congestive heart failure, fibrotic disease, cachexia, graft rejection, cancer, autoimmune disease, rheumatoid arthritis, multiple sclerosis, radiation damage, toxicity following administration of immunosuppressive monoclonal antibodies such as OKT3 or CAMPATH-1 and hyperoxic alveolar injury.

Current clinical ant-TNF strategies involve the use of cortirosteroids such as dexamethasone, and the use of cyclosporin-A or FK506, which are non-specific inhibitors of cytokine gene transcription. Phosphodiesterase inhibitors such as pentoxyfilline have been shown to be more specific inhibitors of TNF gene transcription (Endres S. (1991) Immunol. 72:56–60, Schandene et al (1992), Immunol. 76:30–34, Alegre M L, et al (1991); Transplantation 52:674–679, Bianco et al (1991) Blood 78:1205–1221). Thalidomide has also been shown to inhibit TNF production by leucocytes (Sampajo et al (1991), J. Exp. Med. 173:699–703). In experimental settings, anti-TNF monoclonal antibodies, soluble TNF receptors and soluble TNF receptor/immunoadhesins have been shown to specifically inhibit the effects of TNF action (Bagby et al (1991) J. Infect. Dis. 163:83–88, Charpentier et al. (1991) Pressemed. 20:2009–2011, Silva et al (1990) J. Infect. Dis. 162:421–427; Franks et al (1991) Infect. Immun. 59:2609–2614, Tracey et al (1987) Nature 330:662–664; Fischer et al (1992) PNAS USA in press, Lesslauer et al (1991) Eur. J. Immunol. 21;2883–2886, Ashkenazi et al (1991) PNAS USA 88:10535–10539).

It has recently been shown that the effects of TNF are mediated by two peptides, TNFα and TNFβ. Although these peptides have only 30% homology with each other, they activate the same receptors and are encoded by immediately adjacent genes. As used herein, the term tumour necrosis factor or TNF therefore means tumour necrosis factor α and peptides having a high degrees of sequence homology with, or substantially similar physiological effects to, TNFα, for example TNFβ.

One of the objectives of the present invention is to provide compounds which substantially inhibit the release of TNF from cells, and therefore may be used in the treatment of conditions mediated by TNF. Such uses include, but are not limited to, the treatment of inflammation, fever, cardiovascular effects, hemorrhage, coagulation and acute phase response, cachexia and anorexia, acute infections, shock states, graft versus host reactions and autoimmune disease.

Compounds which have the property of inhibiting the action of metalloproteinases involved in connective tissue breakdown such as collagenase, stromelysin and gelatinase have been shown to inhibit the release of TNF both in vitro and in vivo (AJH Gearing et al (1994), Nature, 370:555–557; G M McGeehan et al (1994), Nature, 370:558–561; WO 93/20047). All of these reported inhibitors contain a hydroxamic acid zinc binding group.

As appreciated by those of skill in the art the significant proportion of homology between human fibroblast collagenase, stromelysin and gelatinase leads to the possibility that a compound that inhibits one enzyme may to some degree inhibit all of them.

Compounds that inhibit collagenase include those encompassed by U.S. Pat. No. 4,511,504 issued Apr. 16, 1985 and U.S. Pat. No. 4,568,666, issued Feb. 4, 1986. Compounds of related structure that are claimed to inhibit stromelysin (proteoglycanase) are encompassed by U.S. Pat. No. 4,771,037, issued Sep. 13, 1988.

It is believed that stromelysin and collagenase inhibitors may have utility in preventing articular cartilage damage associated with septic arthritis. Bacterial infections of the joints can elicit an inflammatory response that may then be perpetuated beyond what is needed for removal of the infective agent resulting in permanent damage to structural components. Bacterial agents have been used in animal models to elicit an arthritic response with the appearance of proteolytic activities. See J. P. Case et al (1989), J. Clin. Invest., 84:1731–40; R. J. Williams et al (1990), Arth. Rheum. 33: 533–41.

It is believed that inhibitors of stromelysin, collagenase and gelatinase may be useful to control tumour metastasis, optionally in combination with current chemotherapy and/or radiation. See L. M. Matrisian et al (1986), Proc. Natl. Acad. Sci., USA, 83;9413–7; S. M. Wilhelm et al (1987), Ibid. 84:6725–29; Werb et al (1989), J. Cell Biol., 109:872–889; L. A. Liotta et al (1983), Lab. Invest., 49:636–649; Reich et al in Metatasis, Ciba Foundation Symposium, Wiley, Chicester, 1988, pp. 193–210.

Secreted proteinases such as stromelysin, collagenase and gelatiase play an important role in processes involved in the movement of cells during metastasic tumour invasion. Indeed, there is also evidence that the matrix metalloproteinases are overexpressed in certain metastatic tumour cell lines. In this context, the enzyme functions to penetrate underlying basement membranes and allow the tumour cell to escape from the site of primary tumour formation and enter the circulation. After adhering to blood vessel walls, the tumour cells use these same metaloprotinases to pierce underlying basement membranes and penetrate other tissues, thereby leading to tumour metastasis. Inhibition of this process would prevent metastasis and improve the efficacy of current treatments with chemotherapeutics and/or radiation.

These inhibitors should also be useful for controlling periodontal diseases, such as gingivitis. Both collagenase and stromelysin activities have been isolated from fibroblasts derived from inflamed gingiva (Uitto et al (1981), J. Periodontal Res., 16:417–424). Enzyme levels have been correlated to the severity of gum disease; C. M. Overall et al (1987), J. Periodontal Res., 22:81–88.

Proteolytic processes have also been observed in the ulceration of the cornea following alkali burns (S. I. Brown et al (1969), Arch. Opthalmol., 81:370–373). Mercapto-containing peptides do inhibit the collagenase isolated from alkali-burned rabbit cornea (F. R. Burns et al (1989), Invest. Opthalmol, 30:1569–1575). Treatment of alkali-burned eyes or eyes exhibiting corneal ulceration as a result of infection with inhibitors of these metalloendoproteinases in combination with sodium nitrate or sodium ascorbate and/or antimicrobials may be effective in preventing developing corneal degradation.

Stromelysin has been implicated in the degradation of structural components of the glomerular basement membrane (GBM) of the kidney, the major function of which is to restrict passage of plasma proteins into the urine (W. H. Baricos et al (1989), Biochem. J., 254:609–612). Proteinuria, a result of glomerular disease, is excess protein in the urine caused by increased permeability of the GBM to plasma proteins. The underlying causes of the increased GBM permeability are unknown, but proteinases including stromelysin may play an important rote in glomerular diseases. Inhibition of this enzyme may alleviate the proteinura associated with kidney malfunction.

It is suggested that inhibition of matrix metalloproinase activity may prevent the rupturing of atherosclerotic plaques leading to coronary thrombosis. The tearing or rupture of atherosclerotic plaques is the most common event initiating coronary thrombosis. Destabilisation and degradation of the connective tissue matrix surrounding these plaques by proteolytic enzymes or cytolines released by infiltrating inflammatory cells has been proposed as a cause of plaque fissuring. Such tearing of these plaques can cause an acute thrombolytic event as blood rapidly flows out of the blood vessel. High levels of stromelysin RNA message have been found to be localized to individual cells in atherosclerotic plaques removed from heart transplant patients at the time of surgery (A. M. Henney et al (1991), Proc. Nat'l, Acad. Sci. USA, 88:8154–8158). Inhibition of stromelysin by these compounds may aid in preventing or delaying the degradation of the connective tissue matrix that stabilizes the atherosclerotic plaques, thereby preventing events leading to acute coronary thrombosis.

It has been recently shown in a model of congestive heart failure (CHF) in the pig, that during CHF there are marked changes in the morphological structure of the heart. Ventricular dilation and wall thinning caused by changes to the extracellular matrix results in fewer collagen connections between cardiomyocytes and less total collagen, In such an instance a weaker force of contraction leads to an inefficient ventricular operation. It is believed that specific inhibitors of matrix metalloproteinases will play a key role in stabilizing the extracellular matrix and therefore be important in the treatment and/or prevention of CHF.

It has recently been shown (WO 96/0240) that inhibitors of the matrix metalloproteinases, such as collagenase and stromelysin also inhibit the formation of human soluble CD23. CD23 is a 45 kDa type II integral protein expressed on the surface of a variety of mature cells, including B and T lymphocytes, macrophages, NK cells, Langerhans cells, monocytes, eosinophils and platelets (Delespesse et al (1991), Adv. Immunology, 49:149; Grangette et al (1989), J., Immunol, 143:3580). Several activities have been ascribed to soluble CD23 in man, all of which involve IgE regulation. Particular activities include:

i) antigen presentation
ii) IgE mediated eosinophil cytotoxicity
iii) B cell homing to lymph nodes and the spleen
iv) downreguladon of IgE synthesis Thus, over the excessive production of soluble CD23 has been implicated in the overproduction of IgE, the hallmark of allergic diseases such a3 extrinsic asthma, rhinitis, allergic conjunctivitis, eczema, a topic dermatitis and anaphylaxis (Sutton et al (1993), Nature, 366:421). Elevated levels of soluble CD23 have also been observed in the serum of patients with chronic B lymphocytic leukemia (Safat et al (1988), Blood, 71:94), and in the synovial fluid of patients with rheumatoid arthritis (Chomarat et al (1993), Arthritis and Rheumatism, 36:234).

Recent reports suggest that new enzymes of the MMP family also mediate the shedding of adhesion molecules such as the selections, such as L-selectin, These soluble adhesion molecules are implicated in a number of diseases including cancer, autoimmunity and in the inflammatory response. It has been proposed that once cleaved, the selectin bind to particular ligands and this accounts for their biological activity. Thus, drugs that interfere with or prevent binding of the ligands to the selections will be useful medicaments for treating a variety of the diseases described above. Therefore, it is a yet further objective of the present invention to provide compounds which inhibit the shedding of certain adhesion molecules and thus provide the production of a medicament for the treatment or prophylaxis of disorders such as cancer, autoimmune diseases or inflammatory diseases (such as inflammatory bowel disease and multiple sclerosis).

It is also believed that specific inhibitors of stromelysin and collagenase should be useful as birth control agents. There is evidence that expression of metalloproteinases, including stromelysin and coflagenase, is observed in unfertilized eggs and zygotes and at further cleavage stages and increased at the blastocyst stage of fetal development and with endoderm differentiation (C. A. Brenner et al (1989), Genes & Develop., 3:848–59). By analogy to tumour invasion, a blastocyst may express metalloproteinases in order to penetrate the extracellular matrix of the uterine wall during implantation. Inhibition of stromelysin and collagenase during these early development processes should presumably prevent normal embryonic development and/or implantation in the uterus. Such intervention would constitute a novel method of birth control. In addition there is evidence that coliagenase is important in ovulation processes. In this example, a covering of collagen over the apical region of the follicle must be penetrated in order for the ovum to escape. Collagenase has been detected during this process and an inhibitor has been shown to be effective in preventing ovulation (J. F. Wocssner et al (1989), Steroids, 54:491–499). There may also be a role for stromelysin activity during ovulation (C. K. L. Too et al (1984), Endocrin., 115:1043–1050).

Collagenolytic and stromelysin activity have also been observed in dystrophic epidermolysis bullosa (A. Icronberger et al (1982), J. Invest. Dermatol., 79:208–211; D. Sawamura et al (1991), Biochem. Biophys. Res. Commun., 184:1003–8). Inhibition of metalloendoproteinases should limit the rapid destruction of connective components of the skin.

In addition to extracellular matrix comprising structural components, stromelysin can degrade other in vivo substrates including the inhibitors $\alpha_1$-proteinase inhibitor and may therefore influence the activities of other proteinases such as clastase (P. G. Winyard et al (1991), FEBS Letts., 279,1:91–94). Inhibition of the matrix metalloendoproteinases may potentiate the antiproteinase activity of these endogenous inhibitors.

From recent publications it is evident that several new enzymes of the MMP family have been identified, some of which may be important in disease. Collagenase 3, an enzyme unique to breast carcinoma cells may have utility in breast cancer (JMP Freije et al (1994), J. Biol. Chem., 269 (24): 16766–16773), whilst MT-MMPs, other members of the MMP family have been shown to be a key enzymes in the activation of gelatinase A (H Sato et al (1994), Nature, 370:61–65). Gelatinase A is an important enzyme in the growth and metastasis of tumors (such as defined above).

The degradation of b-Amytoid Pressor Protein (APP) has been shown to generate amyloid plaques, a major constituent of the senile plaques, found in patients with Alzheimers Disease (AD). Two recent publications have identified metalloproteinase enzymes that cleave APP to the amyloid plaque (C R Abraham et al (1994), Biochemistry, 33:192–199; G Huber et al (1994), Biochem. Biophys Res. Comm., 201 (1): 45–53).

As appreciated by those of skill in the art, the significant proportion of homology between these new enzymes and other MMPs leads to the possibility that a compound that inhibits one enzyme may to some degree inhibit these now enzymes. Therefore, inhibitors encompassed in this invention may be useful in the diseases in which these new enzymes are implicated.

It is, therefore, a further objective of this invention to provide compounds which, in addition to inhibiting TNP release, also inhibit the action of MMPs, and hence may be used in the treatment of patients who suffer from conditions mediated by TNF and/or MMPs.

It is therefore, a further objective of the present invention to provide compounds which inhibit the formation of human soluble CD23 for the production of a medicament for the treatment or prophylaxis of disorders such as allergy and autoimmune disease in which the overproduction of soluble CD23 is implicated, such as those described above.

SUMMARY OF THE INVENTION

The invention encompasses novel mercaptoalkylpeptidyl compounds of formula (I) which are useful inhibitors of matrix metalloproteinaes and/or TNFα mediated diseases including degenerative diseases (such as defined above and in WO-A-9611209) and certain cancers.

In a first aspect of the invention there is provided a compound of general formula (I):

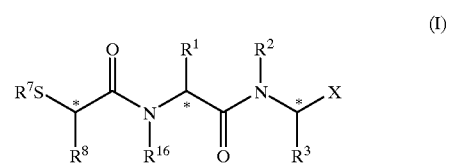

wherein:

$R^1$ may be $C_{1-7}$ alkyl, $C_{2-6}$ alkenyl, $C_{1-6}$ alkyl-aryl, aryl, $C_{1-6}$ alkyl-heteroaryl, heteroaryl or $C_{1-6}$ alkyl-$AR^9$ group where A is O, $NR^9$ or $S(O)_m$ where m=0–2, and $R^9$ is H, $C_{1-4}$ alkyl, aryl, heteroaryl, $C_{1-4}$ alkyl-aryl or $C_{1-4}$ alkyl-heteroaryl; if A=$NR^9$ the groups $R^9$ may be the same or different;

$R^2$ is hydrogen or a $C_{1-6}$ alkyl group;

$R^3$ is a $[Alk]_n R^6$ group where Alk is a $C_{1-6}$ alkyl or $C_{2-6}$ alkenyl group and n is zero or 1;

X is heteroaryl or a group $CONR^4R^5$ where $R^4$ is hydrogen or an $C_{1-6}$ alkyl, aryl, heteroaryl, $C_{1-6}$ alkyl-heteroaryl, cyclo($C_{3-6}$)alkyl, $C_{1-6}$ alkyl-cyclo($C_{3-6}$) alkyl, heterocyclo($C_{4-6}$)alkyl or $C_{1-6}$ alky-heterocyclo ($C_{4-6}$)alkyl group and $R^5$ is hydrogen or a $C_{1-6}$ alkyl group; $NR^4R^5$ may also form a ring such as pyrrolidino, piperidino or morpholino;

$R^7$ is hydrogen or the group $R^{10}CO$ where $R^{10}$ is $C_{1-4}$ alkyl, ($C_{1-4}$ alkyl)aryl, ($C_{1-4}$ alkyl)hoteroaryl, cyclo($C_{3-6}$) alkyl, cyclo($C_{3-6}$) alkyl $C_{1-4}$ alkyl, $C_{2-6}$ alkenyl, $C_{2-6}$ alkenylaryl, aryl or heteroaryl as defined above;

$R^8$ and $R^{16}$ are the same or different and are each $C_{1-4}$ alkyl $R^{11}$, $R^{16}$ may also be H;

$R^6$ represents $AR^9$ or cyclo($C_{3-6}$)alkyl, cyclo($C_{3-6}$) alkenyl, $C_{1-6}$ alkyl, $C_{1-6}$ alkoxyaryl, benzyloxyaryl, aryl, heteroaryl, ($C_{1-3}$ alkyl)heteroaryl, ($C_{1-3}$ alkyl)aryl, $C_{1-6}$ alkyl-$COOR^9$, $C_{1-6}$ alkyl-$NHR^{10}$, $CONHR^{10}$, $NRCO_2R^{10}$, $NHSO_2R^{10}$, $NHCOR^{10}$, amidine or guanidine;

$R^{11}$ is $COR^{13}$ or $NHCOR^{13}$ or the groups

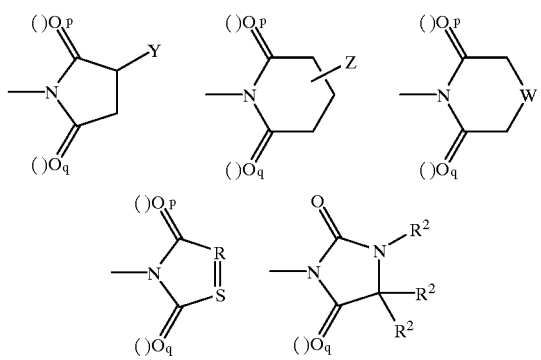

where p and q are each 0 or 1 and are the same or different but when p=q=1, Y cannot be H;

R and S are CH or N and are the sane or different;

W is O, $S(O)_m$ where m=0,1 or 2, or $NR^{12}$;

Y and Z are each H or $C_{0-4}$ alkyl$R^{14}$ wherein $R^{14}$ is $NHR^2$, $N(R^2)_2$ (where each $R^2$ may be the same or different), $COOR^2$, $CONHR^2$, $NHCO_2R^2$ (where $R^2$ is not H), $NHSO_2R^2$ (where $R^2$ is not H) or $NHCOR^2$; Z may be attached to any position on the ring;

$R^{12}$ is hydrogen, $C_{1-4}$ alkyl, $COR^9$, $CO_2R^9$ (where $R^9$ is not H), $CONHR^9$, or $SO_2R^9$ (where $R^9$ is not H);

$R^{13}$ is ($C_{1-4}$ alkyl) $R^{15}$;

$R^{15}$ is $N(R^2)_2$ (where each $R^9$ may be the same or different), $CO_2R^9$, $CONHR^9$, $CON(R^9)_2$ (where each $R^9$ may be the same or different) or $SO_2R^9$ (where $R^9$ is not H), phthalimido or the groups

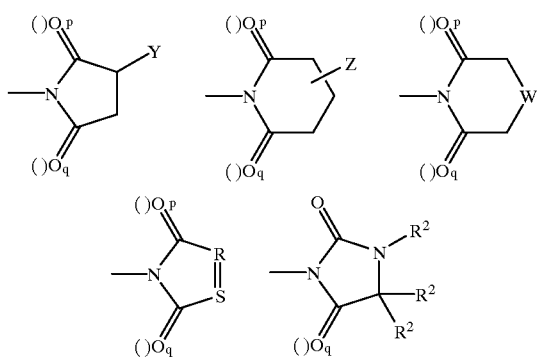

and the salts, solvates and hydrates thereof.

DESCRIPTION OF THE INVENTION

It will be appreciated that the compounds according to the invention can contain one or more asymmetrically substituted carbon atoms, for example those marked with an asterisk in formula (1), The presence of one or more of these asymmetric centres in a compound of formula (1) can give rise to stereoisomers, and in each case the invention is to be understood to extend to all such stereoisomers, including enantiomers and diastereomers, and mixtures including racemic mixtures thereof.

In the formulae herein, the ~ line is used at a potential asymmetric center to represent the possibility of R- and S-configurations, the < line and the . . . line to represent a unique configuration at an asymmetric center.

As used in this specification, alone or in combination, the term "$C_{1-7}$ alkyl" refers to a straight or branched chain alkyl moiety having from one to six carbon atoms, including for example, methyl, ethyl, propyl, isopropyl, butyl, tert-butyl, pentyl, hexyl, heptyl and the like, "$C_{1-6}$ alkyl" means the same, up to 6 carbon atoms, e.g. hexyl, "$C_{1-4}$ alkyl" means the same, up to 4 carbon atoms, e.g. butyl or tert-butyl.

The term "$C_{2-6}$ alkenyl" refers to a straight or branched chain alkyl moiety having two to six carbon atoms and having in addition one double bond, of either E or Z stereochemistry where applicable. This term would include for example, vinyl, 1-propenyl, 1- and 2-butenyl, 2-methyl-2-propenyl etc.

The term "cyclo($C_{3-6}$)alkyl" refers to a saturated alicyclic moiety having from three to six carbon atoms and includes for example cyclopropyl, cyclobutyl, cyclopentyl, cyclohexyl and the like.

The term "cyclo($C_{3-6}$)alkenyl" refers to an alicyclic moiety having from three to six carbon atoms and having in addition one double bond. This term would include for example cyclopentenyl or cyclohexenyl.

The term "heterocyclo($C_{4-6}$)alkyl" refers to a saturated heterocyclic moiety having from four to six carbon atoms and one or more heteroatoms selected from the group N, O, S and includes for example azetidinyl, pyrrolidinyl, tetrahydrofuranyl, piperidinyl and the like.

The term "aryl" means an optionally substituted phenyl or naphthyl group with the substituent(s) being selected, for example, from halogen, trifluoromethyl, $C_{1-6}$ alkyl, alkoxy, phenyl and the like.

The term "halogen" means fluorine, chlorine, bromine or iodine.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a readily cleavable ester such as the methyl, ethyl, benyl or tert-butyl ester.

The term "alkoxy" refers to a straight chain or branched chain alkoxy group containing a maximum of six carbon atoms, such as methoxy, ethoxy, propoxy, isopropoxy, butoxy, tert-butoxy and the like.

The term "heteroaryl" refers to aromatic ring systems of five to ten atoms or which at least one atom is selected from O, N and S and includes for example furanyl, thiophenyl, pyridyl, indolyl, quinolyl and the like.

Salts of compounds of formula (I) include pharmaceutically acceptable salts, for example acid addition salts derived from inorganic or organic acids, such as hydrochlorides, hydrobromides, p-toluenesulphonates, phosphates, sulphats, perchlorates, acetates, trifluoroacetates, propionates, citrates, malonates, succinates, lactates, oxalates, tartes and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically labile ester of formula $CO_2R^{17}$ where $R^{17}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivoyloxymethyl group.

Compounds of the general formula (I) may be prepared by any suitable method known in the art and/or by the following processes, which itself forms part of the invention.

According to a second aspect of the invention, there is provided a process for preparing a compound of general formula (I) as defined above. It will be appreciated that where a patlcular stereoisomer of formula (I) is required, the synthetic processes described herein may be used with the appropriate homochiral stating material and/or isomers maybe resolved from mixtures using conventional seperation techniques (e.g. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, A, B, C, R, S, W, X, Y and Z are as defined above, except where otherwise indicated. It will be appreciated that functional groups, such as amino, hydroxyl or carboxyl groups, present in the various compounds described below, and which it is desired to retain, may need to be in protected form before any reaction is initiated In such instances removal of the protecting group may be the final step in a particular reaction. Suitable protecting groups for such functionality will be apparent to those skilled in the art. For specific details see "Protective Groups in Organic Synthesis", Wiley Interscience, T W Greene, PGM Wutts.

A process for preparing compounds of genera formula (I) comprises deprotecting (for example by hydrolysis) a compound of the formula $R^7S$—$CHR^8$—$CO$—$NR^{16}$—$CHR^1$—$CO$—$NR^2$—$CHR^3$—X (II), wherein $R^7$ represents a suitable protecting group (e.g. tert-butyl, trityl, benzoyl or acetate).

It will be appreciated that where a pancular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I). This is exemplified below.

Intermediates of general formula (II) may be prepared by coupling an acid of the formula $R^7S$—$CHR^8$—$COOH$ (III), wherein $R^7$ and $R^8$ are as defined above, or an active derivative thereof, with an amine of the formula $R^{16}NH$—$CHR^1$—$CO$—$NR^2$—$CHR^3$—X (IV). Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, e.g. a cyclic ether such as tetahydrofuran, an amide e.g. a substituted anide such as dimethylformamide, or a halogenated hydrocarbon such as dichloromethane at a low temperature e.g. −30° C. to ambient temperature, such as −20° C. to 0° C., optionally in the presence of as base, e.g. an organic base such as an amine, e.g. triethylamine or a cyclic amine such as N-methylmorpholine. Where an acid of formula (III) is used, the reaction may additionally be performed in the presence of a condensing agent, for example a diimide such as N,N'-dicyclohexylcabodiimide, advantageously in the presence of a triazole such as 1-hydroxyberotriazole. Alternatively, the acid may be reacted with a chloroformate for example ethylchloroformate, prior to reaction with the amine of formula (IV).

The amine of general formula (IV) may be prepared by coupling an acid of the formula $R^{16}NH$—$CHR^1$—$COOH$ (V), or an active derivative thereof, with an amine of the formula $R^2NH$—$CHX$—$R^3$ (VI) followed by removal of any protecting groups.

Active derivatives of acids of formula (V) include for example acid anhydrides or acid halides such as acid chlorides as outlined earlier.

Amino acids and their derivatives as depicted by general formulae (V) and (VI) can be obtained in chiral or racemic form. In the chiral form they provide asymmetric building blocks for the chiral synthesis of compounds of general formula (I). Many of these derivatives can be readily obtained from commercially available starting materials using methods known to those skilled in the art. (See "The Practice of Peptide Synthesis" by M. Bodanszk et al, Springer Verlag, New York, 1984; WO92/21360).

Compounds of general formula (II) may be prepared by nucleophilic substitution of compounds of the formula $R^8R^{18}C$—$CO$—$NR^{16}$—$CHR^1$—$CO$—$NR^2$—$CHR^3$—X (VII), wherein $R^{18}$ represents a suitable leaving group (e.g. a halogen such as bromide, or an alkylsulphonate ester such as methanesulphonate) with a thiol of the formula $R^7SH$ (VIII), using standard conditions known to those skilled in the art as exemplified in WO 90/05719.

Thiols of formula (VIII) may be obtained from commercially available starting materials using methods known to those skilled in the art. Many thiols of general formula (VIII) are also commercially available.

Compounds of formula (VII) may be prepared by coupling an acid of the formula $R^{18}R^3CH$—$COOH$ (IX), with an amine of formula (IV), wherein $R^{18}$ and $R^8$ are as defined above (or suitably protected versions thereof) or an active derivative thereof, using similar coupling conditions to those described for the preparation of compounds of formula (II).

Carboxylic acids of the structures depicted in formulae (III) and (IX) can be obtained in chiral or racemic form. Many of these derivatives can be readily obtained from commercially available starting materials using methods known to those skilled in the art (see WO 90/05719).

Intermediates of formula (In) may be prepared by coupling an acid of the formula $R^7S$—$CHR^8$—$CO$—$NR^{16}$—$CHR^1$—$COOH(X)$, wherein $R^1$, $R^7$ and $R^8$ are as defined above, or an active derivative thereof, with an amine of formula (VI) by the procedure described previously.

Acids of general formula (X) may in turn be prepared by coupling an acid of formula (III), or an active derivative thereof with an amine of formula (V), or a suitably protected derivative thereof, followed by removal of any protecting groups.

Active derivatives of acids of formula (X) include for example acid anhydrides or acid halides such as acid chlorides as outlined earlier.

Compounds of formula (I) may also be prepared by interconversion of other compounds of formula (I). Thus, for example, a compound of formula (I) wherein $R^1$ is a $C_{1-6}$ alkyl group may be prepared by hydrogenation (using palladium on carbon in suitable solvent, such as an alcohol—e.g. ethanol) of a compound of formula (I) wherein $R^1$ is a $C_{2-6}$ alkenyl group. A further example would include a compound of formula (I) wherein $R^7$ is a group $R^{10}CO$ may be prepared by acylation (using a suitable acid chloride $R^{10}COCl$, in the presence of a base such as a triethylamine in a suitable solvent, such as a chlorinated solvent—eg dichloromethane) of a compound of formula (I) wherein $R^7$ is H.

Compounds where X is heteroaryl may be prepared according to the procedures described in PCT/GB96/01137.

Any mixtures of final products or intermediates obtained can be separated on the basis of the pysicohemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNFα release. The activity and selectivity of the compounds may be determined by use of the appropriate enzyme inhibition test, for example as described in Example A below and in WO-A-9611209. The same publication gives other tests (Examples B to G) appropriate for testing compounds of this invention.

This invention also relates to a method of treatment for patients (including man and/or mammalian animals raised in the dairy, meat or fur industries or as pets) suffering from disorders or diseases which can be attributed to matrix metalloproteinases and/or TNFα as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) am useful in human or veterinary medicine since they are active as inhibitors of TNFα and MMPs. Accordingly in another aspect, this invention concerns:

a method of management (by which is meant treatment or prophylaxis) of disease or conditions mediated by TNFα and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNFα and/or MMPs; and the use of a compound of formula (I) in the preparation of an agent for the management (by which is meant treatment or prophylaxis) of diseases or conditions mediated by TNFα and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, atheroselerosis, congestive heart failure, stroke, vasculitis, Crohn's disease, ulcerative colitis, multiple sclerosis, periodontitis, gingivitis and those involving tissue breakdown such as bone resorption, hydroxy-hemorrhage, coagulation, acute phase response, cachexia and anorexia, acute infections, HIV infections, fever, shock states, graft versus host reactions, dermatological conditions, surgical wound healing, psoriasis, a topic dermatitis, epidermolysis bullosa, tumour growth, angiogenesis and invasion by secondary metastases, ophthalmological disease, retinopathy, corneal ulceration, reperfusion injury, migraine, meningitis, asthma, rhintis, allergic conjunctivitis, eczema and anaphylaxis.

For the treatment of rheumatoid arthritis, osteoarthritis, and in diseases and indications resulting from the overexpression of matrix metalloendoproteinases such as found in certain metastatic tumour cell lines or other diseases mediated by the matrix metalloendoproteinases or increased TNFα production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intranuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs, Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastointestinal tract and thereby provide a sustained action over a longer period. For example, a time delay material such as glyceryl monosteaote or glyeryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcllulose, hydroxypropylmethylcellulose, sodium aiginatc polyvinyl-pyrrolidone, gum tragacanth and gum acacia; dispersing or wetting agents may be a naturally occurring phosphatide, for example lecithin, or condensation products of an allylene oxide with fatty acids, for example polyoxycthylene steantc, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylenc sorbitan monooleate, The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or papania esters derived from fatty acids and hexitot anhydrides, for example sorbitan monooleate and condensation products of the said partial esters with ethylene oxide, for example polyoxyethylene sorkitan monooleate. The emulsions may also contain sweetening and flavoring agents.

Syrups and elixirs may be formulated with sweetening agents, for example gycerol, propylene, glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil mnay be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. For purposes of this application, topical application should include mouth washes and gargles.)

Dosage levels of the order of from about 0.05 mg to about 140 mg per kilogram of body weight per day are useful in the treatment of the above-indicated conditions (about 2.5 mg to about 7 gms per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation Intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The following non-limiting Examples are intended to illustrate the preparation of compounds of Formula (I), and as such are not intended to limit the invention as set forth in the claims.

In the Examples, the following abbreviations are used;

| | |
|---|---|
| $TNF_\alpha$ | Tumour necrosis factor $\alpha$ |
| LPS | Lipopolysaccharide |
| ELISA | Enzyme linked immunosorbent assay |
| RT | Room Temperature |
| EDC | 1-Ethyl-3-(Dimethylaminopropyl)carbodiimide hydrochloride |

INTERMEDIATE 1

[(2R-Bromo-5-phthalimido]pentanoyl-L-leucyl-L-tert-leucine N-methylamide

EDC (1.47 g, 7.71 mmol) was added to a solution of [(2R-bromo-5-phthalimido]pentenoic acid (see WO-A-9611209, intermediate 117, 2.40 g, 7.35 mmol) and N-hydroxybenzotriazole (1.04 g, 7.71 mmol) in tetrahydrofuran (40 ml) at 3° C. L-Leucyl-tert-leucine N-methylamide (see WO-A-9611209, intermediate 116, 1.89 g, 7.35 minol) was added, the mixture was allowed to warm slowly to RT and stirred overnight. The mixture was partitioned between ethyl acetate and water and the aqueous phase was extracted with ethyl acetate. The combined organic phases were washed with 1N HCl, sat. sodium bicarbonate solution and brine, dried ($MgSO_4$) and evaporated in vacuo to give the title compound (3.93 g, 95%) as a white foam which was used in the next step without further purification.

TLC $R_f$ 0.25 (5% MeOH—$CH_2Cl_2$)

INTERMEDIATE 2

[(2S)-Triphenylmethylsulfanyl-5-phthalimido] pentanoyl-L-leucyl-tert-leucine N-methyharide Potassium tert-butoxide (677 mg, 6.03 mmol) was added to a st solution of triphenylmethylmercaptan (1.66 g, 6.03 mmol) in dimethylfornamide (70 ml) at 3° C. After stirring for 20 min intermediate 1 (3.25 g, 5.75 mmol) was added and the mixture was allowed to warm slowly to RT and stirred overnight. The mixture was then poured into water (200 mnl) and the resulting precipitate, collected by filtration and dried in vacuo to give the title compound (3.12 g, 71%) as a pale yellow solid.

TLC $R_f$ 0.47 (5% MeOH—$CH_2Cl_2$)

INTERMEDIATE 3

[(2,S)-Triphenylmethylsulfanyl-5-amino]pentanoyl-L-leucyl-L-tert-leucine N-methylamide 40% aqueous methylamine solution (10 ml, 116 mmol) was added to a solution of intermediate 2 (1.13 g, 1.48 mmol) in methanol (20 ml) at RT. The resulting suspension was stirred at RT overnight. The solvent was evaporated in vacuo, the residue dissolved in ethyl acetate and washed with water and brine, dried ($MgSO_4$) and evaporated in vacuo to give the title compound (850 mg, 91%) as an orange foam.

TLC $R_f$ 0.27 (5% MeOH—$CH_2Cl_2$)

INTERMEDIATE 4

[(2S)-Triphenylmethylsulfanyl-5-[(N,N-dimethylamino)acetyl]amino pentanoyl-L-Ieucyl-L-tert-leucine N-methylamide EDC (65 mg, 0.34 mmol) was added to a stirred solution of interediatc 3 (200 mg, 0.32 mmol), N,N-dimethylglycine (33 mg, 0.32 mmol) and N-hydroxybenzotriazole (46 mg, 0,34 mmol) in tetrahydrofuran (15 ml) at 3° C. The mixture was allowed to warm slowly to RT and stirred overnight. The mixture was then partitioned between ethyl acetate and water and the aqueous phase extracted with ethyl acetate. The combined organic extracts were washed with sat. sodiumn bicarbonate solution and brine, dried ($MgSO_4$) and evaporated in vacuo to give the crude product as a colorless oil. Purification by flash column chromatography, diluting with 2–3% methanol-dichloromethane, provided the title compound (163 mg, 0.23 mmol, 71%) as a white solid.

TLC $R_f$ 0.36 (5% MeOH—$CH_2Cl_2$)

Similarly prepared was:

INTERMEDIATE 5

[(2S)-Triphenylmethylsulfanyl-5-[[N-methyl-N-(1,1-dimethylethoxy carbonyl]aminoacetyl] aminopentanoyl-L-leucyl-L-tert-leucine N-methylamide From intermediate 3 (250 mg, 0.40 mamol), N-(1,1-dimethylethoxycarbonyl)sarcosine (76 mg, 0.40 mmol), EDC (77 mg, 0.40 mmol) and N-hydroxybenzwtriazole (54 mg, 0.40 mmol). The crude product was obtained as a colouless oil. Purification by flash column chromatography, eluting with 2–3% methanol-dichloromethane, provided the title compound (260 mg, 0.32 mmol, 81%) as a white solid.

TLC $R_f$ 0.47 (5% MeOH—$CH_2Cl_2$)

INTERMEDIATE 6

Tert-Butyl 5-bromobutyrate

Boron trifluoride etherate (2 ml) was added to a mixture of 5-bromobutyric acid (8.3 g, 50 mmol) and tert-butyl 2,2,2-trichloroacetimidate (10.5 g, 50 mmol) in dichloromethane (15 ml) and hexane (50 ml) at RT. The mixture was stirred at RT for a further 18 h, then quenched by addition of sodium bicarbonate (5 g). The mixture was then filtered through Celite and the filtrate evaporated in vacuo to provide the title compound (7.2 g, 64%) as a colorless oil.

TLC $R_f$ 0.72 (25% Ether-Hexane).

INTERMEDIATE 7

1,5,5-Trimethyl-3-(3-tert-butoxycarbonylpropyl) hydantoin

Sodium hydride (60%, 1.3 g, 32 mmol) was added to a solution of 1,5,5-trimethylhydantion (4.0 g, 28.2 mmol) in dimethylformamide (10 ml) at 0° C. and the mixture was stirred under nitrogen for 30 min. A solution of intermediate 7 (7.1 g) was then added, and the resulting mixture was stirred overnight at RT, then poured into water (100 ml) and extracted with tert-butyl methyl ether (100 ml). The organic phase was washed with water and brine, dried ($MgSO_4$) and evaporated in vacuo to furnish the tide compound (3.7 g, 46%) as a colorless oil.

TLC $R_f$ 0.25 (2:1 Ether-Hexane)

INTERMEDIATE 8

1,5,5-Trimethyl-3-(3-carboxypropyl)hydantoin

Trifluoroacetic acid (10 ml) was added to a solution of intermediate 7 (3.6 g) in dichloromethane (10 ml) at RT and the solution was stirred for 18 h. The resulting solution was evaporated in vacuo and the residual trifluoroacetic acid was azeotroped with toluene (3×50 ml) to give provide the title compound as colorless viscous oil, which was used directly in the next step.

TLC $R_f$ 0.45 (Ether).

INTERMEDIATE 9

1,5,5-Trimethyl-3-(3-bromo-3-carboxypropyl) hydantoin

A solution of the crude intermediate 8 was stirred in dichloroethane (10 ml) containing thionyl chloride (1.1 ml) for 3 h, then heated to 80° C. for 30 min. Phosphorus trichloride (0.11 ml) was added, followed by bromine (2.5 g) and the mixture heated at 80° C. for 3 h. The solution was then cooled, water (10 ml) was cautiously added and the biphasic mixture was stirred at 50° C. for 72 h. Further water (100 ml) was then added and the mixture basified with sodium bicarbonate, then washed with ether, The aqueous phase was acidified with 2M hydrochloric acid to pH 2 and the mixture extracted with dichloromethane. The combined extracts were dried ($MgSO_4$) and evaporated in vacuo to provide the title compound (3.5g, 87%), as a colorless viscous oil.

TLC $R_f$ 0.45 (Ether).

INTERMEDIATE 10

1,5,5-Trmethyl-3-(3-acetylthio-3-carboxypropyl) hydantoin

A solution of intermediate 10 (3.5 g) in methanol (20 ml) was treated with potassium thioacetate (1.56 g) at RT. The mixture was then stind for 18 h, evaporated in vacuo and the residue partitioned between 0.5M hydrochloric acid and dichloromethane. The organic phase was washed with water and brine, dried ($MgSO_4$) and evaporated in vacuo to give the title compound (3.0 g, 88%) as an orange solid.

TLC R$_f$ 0.52 (Ether).

The following were prepared, according to the procedure outlined for L-Leucyl-L-tert-leucine N-methylamide (intermediate 116 in WO-A-9611209)

INTERMEDIATE 11

L-(S-Methyl)cysteinyl-L-Leucyl-L-tert-leucine N-methyiamide

INTERMEDIATE 12

L-Norvalinyl-L-tert-leucine N-methylamide

EXAMPLE 1

[(2S)-Sulfanyl-5-[(N,N-dimethylamino)acetyl] aminopentanoyl-L-leucyl-L-tert-leucine N-mnethylamide Intermediate 4 (150 mg, 0.21 mmol) was dissolved in a mixture (10 ml) of trifluoroacetic acid (90%), thioanisole (5%), triisopropylsilane (2.5%) and water (2.5%) and the solution was stir at RT overnight. The volatiles were evaporated in vacuo to give the crude product as a yellow solid. Purification by flash column chromatography on silica, diluting with 2–3% methanol-dichloromethane, provided the title compound (59 mg, 0.12 mmol, 59%) as a white solid.

TLC R$_f$ 0.30 (5% MeOH—CH$_2$Cl$_2$)

Similarly prepared was:

EXAMPLE 2

[(2S)-Sulfanyl-5-[(N-methylamino)acetyl] aminopentanoyl-L-leucyl-L-tert-leucine N-methylamide From intermediate 5 (220 mg, 0.27 mmol). The crude product was obtained as a yellow solid. Purification by flash column chromatography, eluting with 2–3% methanol-dichloromethane, provided the title compound (92 mg, 0.16 mmol, 59%) as a white solid.

TLC R$_f$ 0.21 (5% MeOH—CH$_2$Cl$_2$)

EXAMPLE 3

N-[2-(Acetylthio)-4-(1,5,5-trimethylhydantoinyl) butanoyl]-L-Leucyl-L-tert-leucine N-methylamide A solution of L-leucyl-L-tert-leucine N-methylamide (0.4 g) and intermediate 10 (0.4 g) in dichloromethane (20 ml) was treated with EDC (0.3 g) and the mixture stirred for 18 h at RT. The solution was washed with 0.5M hydrochloric acid and sodium bicarbonate, dried (MgSO$_4$) and evaporated in vacuo to provide the title compound (65%) as a beige foam.

TLC R$_f$ 0.42 (10% MeOH—CH$_2$Cl$_2$)

EXAMPLE 4

N-[2-(Acetylthio)-4-(1,5,5trimethylhydantoinyl) butanoyl]-L-(S-methyl)cysteinyl-L-tert-leucineN-methylamide From intermediate 10 and intermediate 11, as a beige foam (73%).

TLC R$_f$ 0.37 (10% MeOH—CH$_2$Cl$_2$)

EXAMPLE 5

N-[2-(Acetylthio)-4-(1,5,5-trimethylhydantoinyl) butanoyl]-L-norvalinyl-L-tert-leucine N-methylamide From intermediate 10 and intermediate 12, as a beige foam (68%).

TLC R$_f$ 0.35 (10% MeOH—CH$_2$Cl$_2$)

EXAMPLE 6

N-[2-Sulphanyl-4(1,5,5-Trimethylhydantoinyl) butanoyl]-L-leucine-L-tert-leucine N-methylamnide A solution of example 3 (0.4 g) in methanol (10 ml) was treated with ammonium hydroxide (SG 0.88, 1 ml) at RT for 3 h. The mixture was evaporated in vacuo, partioned between dichlorormethane and water, dried (MgSO$_4$) and evaporated in vacuo to provide the crude product as a beige solid. The residue was purified by flash column chromoatography on silica, eluting with 5% methanol in dichloromethane to provide the title compound (0,35 g, 83%), as a colourless solid.

TLC R$_f$ 0.35 (10% MeOH—CH$_2$Cl$_2$)

EXAMPLE 7

N-[2-Sulphanyl-4-(1,5,5-trimethylhydantoinyl) butanoyl]-L-(S-methyl)cysteinyl-L-tert-leucine N-methylamide From example 5, as a colourless solid (85%)

EXAMPLE 8

N-[2-Sulphanyl-4-(1,5,5,trimethylhydantoinyl) butanoyl]-L-norvalinyl-L-tert-leucine N-methylamide From example 6, as a colourless solid (88%)

EXAMPLE A

Collagenase Inhibition Activity

The potency of compounds of general formula (I) to act as inhibitors of collagenase was determined by the procedure of Cawston and Barrett, (Anal. Biochem., 99:340–345, 1979) whereby a 1 mM solution of the inhibitor being tested or dilutions thereof was incubated at 37° C. for 16 hours with collagen and collagenase (buffered with 50 mM Tris, pH 7.6 containing 5 mM CaCl$_2$, 0.05% Brij 35, 60 mM NaCl and 0.02% NaN$_3$). The collagen was acetylated $^3$H or $^{14}$C-collagen prepared by the method of Cawston and Murphy (Methods in Enzymology, 80:711, 1981). The choice of radiolabel did not alter the ability of collagenase to degrade the collagen substrate. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitor and the results reported as that inhibitor concentration effecting 50% inhibition of the collagenase (IC$_{50}$).

EXAMPLE B

Stromelysin Inhibition Activity

The potency of compounds of general formula (I) to act as inhibitor of stromelysin was determined using the procedure of Nagase et al (Methods in Enzymology Vol 254, 1994), whereby a 0.1 mM solution of the inhibitor being tested or dilutions thereof was incubated at 37° C. for 16 hours with stromelysin and $^3$H transferrin (buffered with 50 mM Tris, pH 7.6 containing 10 mM CaCl$_2$, 150M NaCl, 0.05% Brij, 35, and 0.02% NaN$_3$). The transferrin was carboxymethylated with $^3$H iodoacetic acid. The stromelysin activity in the presence of 1 mM, or a dilution thereof, was compared to activity in a control devoid of inhibitor and the results reported as that inhibitor concentration effecting 50% inhibition of the stromielysin ($IC_{50}$)

EXAMPLE C
Gelatinase Inhibition Activity

The potency of the compounds of general formula (I) to act as inhibitors of gelatinase was determined using the procedure of Harris & Kruane (Biochem Biophys. Acta, 258:566–576, 1972), whereby a 1 mM solution of the inhibitor being tested or dilutions thereof was incubated at 37° C. for 16 hours with gelatinase and heat denatured $^3$H or $^{14}$C-acetylated collagen (buffered with 50 mM Tris, pH 7.6 containing 5 mM $CaCl_2$, 0.05% Brij 35 and 0.02% $NaN_3$). The $^3$H or $^{14}$C gelatin was prepared by denaturing $^3$H or $^{14}$C-collagen produced according to the method of Cawston and Murphy (Methods in Enzymology, 80:711, 1981) by incubation at 60° C. for 30 minutes. Undigested gelatin was precipitated by addition of trichloroacetic acid and centrifugation. The gelatinase activity in the presence of 1 mM, or dilution thereof, was compared to the activity in a control devoid of inhibitor and results reported as that inhibitor concentration effecting 50% inhibition of the gelatinase ($IC_{50}$).

EXAMPLE D
MMP Inhibition Activity-Fluorimetric Assay

The potency of compounds of general formula (I) to act as inhibitors of collagenase-1(MMP-1), collagenase-2 (MMP-8), gelatinase-A (MMP-2), gelatinae-B (MMP-9) and stromelysin-1(MMP-3) was determined using the following procedure; Inhibitors are dissolved in dimethylsulphoxide containing 0.02% b-mercaptoethanol and serial dilutions are prepared. Activated enzyme is incubated in assay buffer containing 50 mM Tris, pH 7.4, 5 mM $CaCl_2$, 0.002% $NaN_3$ and Brij 35 in the presence and absence of inhibitor. Samples are preincubated at 37° C. for 15 minutes before the addition of the fluorimetric substrate (Mca-Pro-Leu-Dpa-Ala-Arg-$NH_2$) to a final concentration of 10 mM. The assay is incubated for 90 minutes at 37° C. and then read in a Fluoroscan II at $1_{ex}$ (355 nm) and $1_{exes}$ (460 nm).

The enzyme activity was compared to activity in a control devoid of inhibitor and the results reported as that inhibitor concentration effecting 50% inhibition of the stromelysin ($IC_{50}$).

EXAMPLE E
Inhibition of TNFα Production

The potency of the compounds of general formula (I) to act as inhibitors of the production of TNFα was determined using the following procedure. A 1 mM solution of the inhibitor being tested or dilutions thereof was incubated at 37° C. in an atmosphere of 5% $CO_2$ with THP-1 cells (human monocytes) suspended in RPM1 1640 medium and 20 μM β-mercaptoethanol at a cell density of 1×10$^6$/ml and stimulated with 5 μg/ml final concentration of LPS. After 18 hours the supernatant is assayed for the levels of TNFα using a commercially available ELISA kit (R & D Systems).

The activity in the presence of 0.1 mM inhibitor or dilutions thereof was compared to activity in a control devoid of inhibitor and results reported as that inhibitor concentration effecting 50% inhibition of the production of TNFα.

EXAMPLE F
Adjuvant Arthritic Rat Model

Compounds of general formula (I) were evaluated in an adjuvant arthritis model in the rat based on the methods employed by B. B. Newbould (1963), Br. J. Pharmacol, 21, 127–136 and C. M. Pearson and F. D. Wood (1959), Arthritis Rheum, 2, 440–459. Briefly male Wistar rats (180–200 g) were injected at the base of the tail with Freund's adjuvant. Twelve days later the responding animals were randomized into experimental groups. Compounds of general formula (I) were dosed either orally as a suspension in 1% methyl cellulose or intraperitoneally in 0.2% carboxymethylcellulose from day 12 to the end of the experiment on day 22. Hind paw volumes were measured every two days from day 12 onwards and X-rays were taken of the hind feet on completion of the experiment. Results were expressed as the percent increase of foot volume over day 12 values.

EXAMPLE G
Mouse Ovarian Carcinoma Xenograft Model

Compounds of general formula (I) were evaluated in an ovarian carcinoma xenograft model of cancer, based on that described by B. Davies et al (1993), Cancer Research, 53, 2087–2091. This model, in brief, consists of inoculating female nu/nu mice with 1×10$^9$ OVCAR3-icr cells into the peritoneal cavity. Compounds of general formula (I) are administered by the oral route as a suspension in 1% methyl cellulose or intraperitoneally as a suspension in phosphate buffered saline in 0.01% Tween-20. At the conclusion of the experiment (4–5 weeks) the number of peritoneal cells are counted and any solid tumour deposits weighed. In some experiments tumour development is monitored by measurement of tumour specific antigens.

EXAMPLE H
Rat Mammary Carcinoma Model

Compounds of general formula (I) were evaluated in a HOSP.1 rat mammary carcinoma model of cancer (S. Eccles et al (1995), Cancer Research, in press). This model consists of the intravenous inoculation of female CBH/cbi rats with 2×10$^4$ tumour cells into the jugular vein. Compounds of general formula (I) are administered by the oral route as a suspension in 1% methyl cellulose or intraperitoneally as a suspension in phosphate buffered saline in 0.01% Tween-20. At the conclusion of the experiment (4–5 weeks) the animals were killed, the lungs were removed and individual tumors counted after 20 hours fixation in Methacarn.

We claim:

1. A compound of general formula (I):

$$R^7S-\overset{O}{\underset{*}{C}}-\underset{\underset{R^8}{|}}{\overset{}{N}}-\overset{R^1}{\underset{*}{C}}-\overset{}{\underset{R^{16}}{N}}-\overset{O}{\underset{}{C}}-\overset{R^2}{\underset{*}{N}}-\overset{}{\underset{R^3}{C}}-X$$ (I)

$R^1$ is $C_{1-7}$ alkyl, $C_{2-6}$ alkenyl, $C_{1-6}$ alkyl-aryl, aryl, $C_{1-6}$ alkyl-heteroaryl, heteroaryl or $C_{1-6}$ alkyl-$AR^9$ group where A is O, $NR^9$ or $S(O)_m$ where m=0–2, and $R^9$ is H, $C_{1-4}$ alkyl, aryl, heteroaryl, $C_{1-4}$ alkyl-aryl or $C_{1-4}$ alkyl-heteroaryl; if A=$NR^9$ the groups $R^9$ may be the same or different, $R^2$ is hydrogen or a $C_{1-6}$ alkyl group;

$R^3$ is a $R^6$ group where Alk is a $C_{1-6}$ alkyl or $C_{2-6}$ alkenyl group and n is zero or 1;

X is heteroaryl or a group $CONR^4R^5$ where $R^4$ is hydrogen or an $C_{1-6}$ alkyl, aryl, heteroaryl, $C_{1-4}$ alkyl-heteroaryl, cyclo($C_{3-6}$)alkyl, $C_{1-6}$ alkyl-cyclo($C_{3-6}$) alkyl, heterocyclo($C_{4-6}$)alkyl or $C_{1-6}$ alkyl-heterocyclo ($C_{4-6}$)alkyl group and $R^5$ is hydrogen or $C_{1-6}$ alkyl; $NR^4R^5$ may also form a ring;

$R^7$ is hydrogen or the group $R^{10}$ CO where $R^{10}$ is $C_{1-4}$ alkyl, ($C_{1-4}$alkyl)aryl, ($C_{1-6}$alkyl)heteroaryl, cyclo ($C_{3-6}$) alkyl, cyclo($C_{3-6}$)alkyl-$C_{1-4}$ alkyl, $C_{2-6}$ alkenyl, $C_{2-6}$ alkenylaryl, aryl or heteroaryl;

$R^8$ and $R^{16}$ are the same or different and are each $C_{1-4}$ alkyl $R^{11}$, $R^{16}$ may also be H;

$R^6$ represents $AR^9$ or cyclo($C_{3-6}$)alkyl, cyclo($C_{3-6}$) alkenyl, $C_{1-6}$ alkyl, $C_{1-6}$ alkoxyaryl, benzyloxyaryl, aryl, heteroaryl, ($C_{1-3}$ alkyl)heteroaryl, ($C_{1-3}$ alkyl)aryl, $C_{1-6}$ alkyl-COOR$^9$, $C_{1-6}$ alkyl-NHR$^{10}$, CONHR$^{10}$, NHCO$_2$R$^{10}$, NHSO$_2$R$^{10}$, NHCOR$^{10}$, amidine or guanidine;

$R^{11}$ is COR$^{13}$, NHCOR$^{13}$ or any of the groups

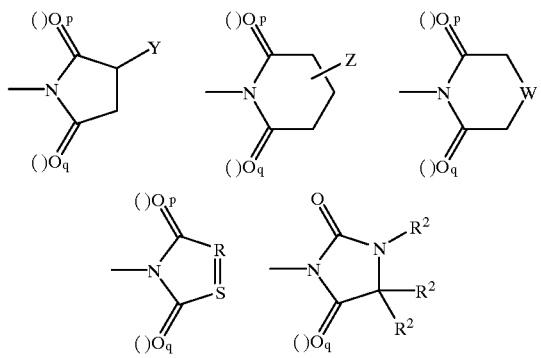

where p and q are each 0 or 1 and are the same or different but when p=q=1, Y cannot be H;

R and S are each CH or N and are the same or different;

W is O, S(O)$_m$ where m=0,1 or 2 or NR$^{12}$;

Y and Z are each H or $C_{0-4}$ alkylR$^{14}$ wherein $R^{14}$ is NHR$^2$, N(R$^2$)$_2$ (where each R$^2$ may be the same or different), COOR$^2$, CONHR$^2$, NHCO$_2$R$^2$ (where R$^2$ is not H), NHSO$_2$R$^2$ (where R$^2$ is not H) or NHCOR$^2$; Z may be attached to any position on the ring;

$R^{12}$ is hydrogen, $C_{1-4}$ alkyl, COR$^9$, CO$_2$R$^9$ (where R$^9$ is not H), CONHR$^9$, or SO$_2$R$^9$ (where R$^9$ is not H);

$R^{13}$ is ($C_{1-4}$ alkyl)R$^{15}$;

$R^{15}$ is N(R$^2$)$_2$ (where each R$^9$ may be the same or different), CO$_2$R$^9$, CONHR$^9$, CON(R$^9$)$_2$ (where each R$^9$ may be the same or different) or SO$_2$R$^9$ (where R$^9$ is not H), phthalimido or the groups

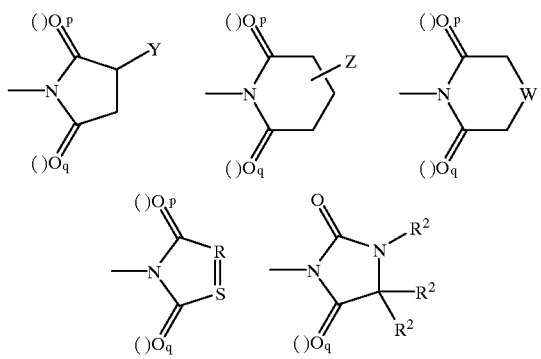

as defined above;

and the salts, solvates and hydrates thereof.

2. The compound of claim 1, wherein X is CONR$^4$R$^5$; $R^4$ is H, alkyl or aryl; $R^6$ is not amidine or guanidine; $R^{11}$ is not NHCOR$^{13}$ or the last of the given groups; $R^{15}$ is not N(R$^2$)$_2$ or the last of the given groups; and $R^{16}$ is H.

3. The compound of claim 1 selected from the group consisting of

[(2S)-Sulfanyl-5-[(N,N-dimethylamino)acetyl] aminopentanoyl-L-leucyl-L-tert-leucine N-methylamide; and

[(2S)-Sulfanyl-5-[(N-methylamino)acetyl]aminopentnoyl-L-leucyl-L-tert-leucine N-methylamide.

4. The compound of claim 1 selected from the group consisting of

[(2S)-Acetylthio)-4(1,5,5-trimethylhydantoinyl)butanoyl]-L-Leucyl-L-tert-leucine N-methylamide;

[(2S)-Acetylthio)-4(1,5,5-trimethylhydantoinyl)butanoyl]-L-(S-methyl)cysteinyl-L-tert-leucine N-methylamide;

[(2S)-Acetylthio)-4(1,5,5-trimethylhydantoinyl)butanoyl]-L-norvalinyl-L-tert-leucine N-methylamide;

N-[2-Sulfanyl-4-(1,5,5-trimethylhydantoinyl)butanoyl]-L-leucyl-L-tert-leucine N-methylamide;

N-[2-Sulfanyl-4-(1,5,5-trimethylhydantoinyl)butanoyl]-L-(S-methyl)cysteinyl-L-tert-leucine N-methylamnide; and N-[2-Sulfanyl-4-(1,5,5-trimethylhydantoinyl)butanoyl]-L-norvalinyl-L-tert-leucine N-methylamide.

5. The compound of any preceding claim in the form of a single enantiomer or diastercoiner, or a mixture of such isomers.

6. The compound of claim 1, wherein the ring formed from NR$^4$R$^5$ is pyrrolidino, piperidino or morpholino.

7. A pharmaceutical composition comprising a compound of claim 1, and a pharmaceutically-acceptable diluent or carrier.

8. The pharmaceutical composition according to claim 7, wherein said pharmaceutical composition is formulated to be administered to a human or animal by a route selected from the group consisting of oral administration, topical administration, parenteral administration, inhalation administration and rectal administration.

9. A method for the treatment in a human or animal of a condition associated with matrix metalioproteinases or that is mediated by TNFα or L-selectin sheddase, wherein said method comprises the administration of an effective amount of a compound of claim 1 to said human or animal.

10. The method according to claim 9, wherein said condition is selected from the group consisting of cancer, inflammation and inflammatory diseases, tissue degeneration, periodontal disease, ophthalmological disease, dermatological disorders, fever, cardiovascular effects, hemorrhage, coagulation and acute phase response, cachexia and anorexia, acute infection, HIV infection, shock states, graft versus host reactions, autoimmune disease, reperfusion injury, meningitis and migraine.

11. The method according to claim 9, wherein said condition is selected from the group consisting of tumour growth, angiogenesis, tumour invasion and spread, metastases, malignant ascites and malignant pleural effusion.

12. The method according to claim 9, wherein said condition is selected from the group consisting of rheumatoid arthritis, osteoporosis, asthma, multiple sclerosis, neurodegeneration, Alzheimer's atheroselerosis, stroke, vasculitis, Crohn's disease and ulcerative colitis.

13. The method according to claim 9, wherein said condition is selected from the group consisting of corneal ulceration, retinopathy and surgical wound healing.

14. The method according to claim 9, wherein said condition is selected from the group consisting of psoriasis, atopic dermatitis, chronic ulcers and epidermolysis bullosa.

15. The method according to claim 9, wherein said condition is selected from the group consisting of periodontitis and gingivitis.

16. The method according to claim 9, wherein said condition is selected from the group consisting of rhinitis, allergic conjunctivitis, eczema and anaphylaxis.

17. The method according to claim 9, wherein said condition is selected from the group consisting of restonosis, congestive heart failure, endometriosis, atheroselerosis and endoselerosis.

18. The method according to claim 9, wherein said condition is osteoarthritis.

* * * * *

UNITED STATES PATENT AND TRADEMARK OFFICE
CERTIFICATE OF CORRECTION

PATENT NO. : 5,981,490
DATED : November 9, 1999
INVENTOR(S) : Andrew Douglas Baxter, et. al.

It is certified that error appears in the above-identified patent and that said Letters Patent is hereby corrected as shown below:

Column 20, line 63: "$C_{1-4}$ alkyl-heteroaryl" should read --$C_{1-6}$ alkyl-heteroaryl--.

Column 22, line 25: "diastercoiner" should read --diastereomer--.

Column 22, line 39: "metalioproteinases" should read --metalloproteinases--.

Column 24, line 2: "restonosis" should read --restenosis--.

Column 24, line 4: "endoselerosis" should read --endosclerosis--.

Signed and Sealed this

Twenty-seventh Day of February, 2001

Attest:

NICHOLAS P. GODICI

Attesting Officer

Acting Director of the United States Patent and Trademark Office